United States Patent [19]

Kohnert et al.

[11] Patent Number: 5,747,030
[45] Date of Patent: May 5, 1998

[54] PHARMACEUTICAL PREPARATION CONTAINING PLASMINOGEN ACTIVATORS

[75] Inventors: Ulrich Kohnert, Habach; Stephan Fischer, Polling; Hans-Jörg Markl, Ellerstadt; Heinrich Woog, Laudenbach, all of Germany

[73] Assignee: Boehringer Mannheim GmbH, Mannheim, Germany

[21] Appl. No.: 693,226

[22] PCT Filed: Feb. 18, 1995

[86] PCT No.: PCT/EP95/00596

§ 371 Date: Aug. 21, 1996

§ 102(e) Date: Aug. 21, 1996

[87] PCT Pub. No.: WO95/22347

PCT Pub. Date: Aug. 24, 1995

[30] Foreign Application Priority Data

Feb. 21, 1994 [DE] Germany .................... 44 05 426.2

[51] Int. Cl.⁶ ............................ A61K 38/48; A61K 38/54
[52] U.S. Cl. ................... 424/94.64; 424/94.3; 424/94.63

[58] Field of Search ............... 424/94.64, 94.63, 424/94.3, 94.1; 435/188

[56] References Cited

U.S. PATENT DOCUMENTS

| | | | |
|---|---|---|---|
| 5,068,106 | 11/1991 | Paques et al. | 424/94.3 |
| 5,352,452 | 10/1994 | Kohnert et al. | 435/94.64 |
| 5,352,453 | 10/1994 | Kohnert et al. | 435/94.64 |

FOREIGN PATENT DOCUMENTS 1732288  8/1988  Australia .

*Primary Examiner*—Leon B. Lankford, Jr.
*Assistant Examiner*—Christopher R. Tate
*Attorney, Agent, or Firm*—Nikaido Marmelstein Murray & Oram LLP

[57] ABSTRACT

The invention relates to pharmaceutical preparations containing plasminogen activators, sugars and tranexamic acid, in the form of a lyophilisate or an injection or infusion solution. In particular, the preparations contain a sugar, phosphate buffer, tranexamic acid as well as a surfactant and the liquid solutions preferably have a pH value of 5.5–6.5.

29 Claims, No Drawings

PHARMACEUTICAL PREPARATION CONTAINING PLASMINOGEN ACTIVATORS

The invention relates to pharmaceutical preparations containing plasminogen activators or derivatives of same as the active substances and to related pharmaceutical forms of administration in the form of lyophilisates or injection and infusion solutions, respectively.

The human tissue plasminogen activator (t-PA) is of immense therapeutic importance in dissolving blood clots, e.g., in cardiac infarctions. t-PA causes dissolving of blood clots by activation of plasminogen to plasmin. Plasmin, in turn, dissolves fibrin which is the major component of the protein matrix of clotted blood.

Natural t-PA is composed of multiple functional domains F, E, K1, K2, and P. Domain P involves the proteolytically active centre causing cleavage of plasminogen to plasmin. The preparation of plasminogen activators (PA) by genetic engineering, in particular, of t-PA or various t-PA muteins in eukaryotic and prokaryotic cells is already known. Here, in contrast to natural t-PA, t-PA derivatives are synthesised from prokaryotes in non-glycosylised form.

In the meaning of the invention, in principle, such derivatives of t-PA, particularly those prepared by recombination, are possible as the plasminogen activators, which essentially comprise those protein regions of natural protein that are responsible for the fibrinolysis of the thrombi. Here, such t-PA derivatives may also be used which have deletions or substitutions of single or multiple amino acids in the t-PA sequence.

According to the invention, the following plasminogen activators may be employed, for example: t-PA (e.g., Alteplase), LY 210825 (K2P available from "Syrian hamster" cell lines, Circ. 1990, 82, 930–940); ΔFE3x and ΔFE1x (K1K2P, Blood 1988, 71, 216–219); ΔFEK1 (K2P from C127 mouse cells, J. Cardiovasc. Pharmacol. 1990, 16, 197–209); E-6010 (Jap. Circ. J. 1989, 53, p. 918); t-PA variants (Thromb. Haemost. 1989, 62, p. 542); K2P and D-K2P (Thromb. Haemost. 1989, 62, p. 393); MB-1018 (FK2K2P, Thromb. Haemost. 1989, 62, p. 543); FK2P (FASEB J. 1989, 3, A1031, abstract 4791); Δ1x (Circulation 1988, 4, II-15); K1K2P (Thromb. Res. 1988, 50, 33–41); FK1K2P (J. Biol. Chem. 1988, 263, 1599–1602); TNK variant of t-PA (WO 93/24635); bat-PA (Witt et al., Blood 1992, 79, 1213–1217, and Mullot et al., Arterioscler. Thrombos. 1992, 12, 212–221). In particular, those plasminogen activators are possible which contain the cringle 2 domain ("K2") of the t-PA and/or the serine protease domain ("P"). In this respect, one may exemplify the K2P type t-PA mutein "r-PA" described in EP 0 382 174 (WO 90/09437).

More specifically, the present invention relates to K2P, K1K2P, FK1K2P, and FK2K2P type plasminogen activators as described in the following printings: Protein Engineering 5(1), 93–100 (1992); DE-OS-39 23 339.1; Circ. 1990, 82, 930–940; J. Cardiovasc. Pharmacol. 1990, 16, 197–203; Blood 1988, 71, 216–219; J. Biol. Chem. 1988, 263, 1599–1602; Thromb. Haemost. 1989, 62, p. 543. In particular, recombinant K2P type plasminogen activators are employed as described in EP-A-0 382 174 and in Protein Engineering Vol. 5(1), p. 93–100 (1992). Further t-PA muteins of this type are described in the following patent applications: U.S. Pat. No. 4,970,159, EP-A-0 196 920, EP-A-0 207 589, AU 61804/86, EP-A-0 231 624, EP-A-0 289 508, JP 63133988, EP-A-0 234 051, EP-A-0 263 172, EP-A-0 241 208, EP-A-0 292 009, EP-A-0 297 066, EP-A-0 302 456, EP-A-0 379 890.

The substantial influence of the sugar proportion on solubility and aggregation of proteins is known from prior art (J. Biol. Chem. 263 (1988), 8832–8837). Thus, it has been determined in EP-B-458 950 that, e.g., a non-glycosylated recombinant plasminogen activator of domain composition K2P has a substantially poorer solubility than glycosylated t-PA derivatives, for example. As a rule, non-glycosylated plasminogen activators such as r-PA dissolve only to a slight extent in buffers conventionally used for the solubilisation of proteins, such as 50 mmoles/l of Na citrate pH 6, 50 mmoles/l of phosphate buffer or physiological NaCl solution. However, utilisation as a therapeutic agent requires plasminogen activators to be present at sufficiently high concentrations, preferably, at a concentration of up to 10 mg/ml.

Increasing the solubility of t-PA from prokaryotes by neutral or slightly alkaline arginine formulations is known from EP-A-0 217 379. However, this procedure suffers from the drawback that good solubility of t-PA from prokaryotes can only be achieved with very high arginine concentrations.

Further galenic formulations of plasminogen activators or their derivatives are known from WO 90/01333, WO 89/050347, WO 90/08557, EP 0 297 294, EP 0 156 169, and EP 0 228 862.

Thus, WO 90/01333 (Invitron) describes the combination of lysine, histidine, arginine with citrate for t-PA and derivatives from bacteria. Citrate is used at 5 mmoles/l, lysine, histidine, arginine at 150 mmoles/l at pH 6. Furthermore, albumin is added.

WO 89/050347 (Invitron) describes the combination of arginine (20–200 mmoles/l) and citrate (20–80 mmoles/l) at pH 5–8.

WO 90/08557 (Genetics Institute) discloses a combination of creatinine with various additives such as histidine, arginine, proline, betaine, choline, imidazole, tryptophan, citrate, optionally with addition of glutamic acid, aspartic acid and succinic acid.

EP 0 297 294 (Behring) discloses the combination of at least two amino acids such as lysine, ornithine, arginine, tranexamic acid and other additives at pH 5–10.

EP 0 156 169 (Asahi) describes ornithine and/or lysine, optionally with addition of citrate, glycine or phosphate, and EP 0 228 862 (Genentech) discloses a formulation containing arginine with or without chloride and with or without detergent.

Likewise, alternative formulations of r-PA in the presence of lysine and lysine analogues, respectively, in solutions buffered with citric acid are described in EP 0 458 950 (Boehringer Mannheim). However, more recent examinations demonstrate that the solubility of r-PA in these formulations as well, is not as yet completely sufficient. It has been determined that in fact, the solubility may be improved by increasing the citrate concentration; however, such formulations are not or only in part tolerated by the veins. Moreover, the high salt concentrations and the low glass temperature (Tg') associated therewith result in the necessity to carry out the lyophilisation of these formulations at temperatures below −45° C. and −50° C. Technically, these temperatures are realizable often only at a very high expenditure, and they require complex control and monitoring elements in order to control and measure the optimum conditions for lyophilisation. Moreover, this involves a relatively high expenditure of energy. Furthermore, for industrial production there are often used rather old lyophilisation plants, which lack the requisite complex measuring and control technology, and where, consequently, as a rule, there can only be guaranteed a working temperature of about −45° C.

The object of the invention is to provide formulations of plasminogen activators and their derivatives which are well tolerated by the veins, contain the active substance at sufficiently high concentrations and ensure good solubility of the active substance, with the intention of maintaining stability of the PA in the lyophilisate over a prolonged period of time. In addition, the invention is aimed to develop formulations which can be lyophilised reliably on an industrial production scale as well, with the intention of ensuring a well reproducible product quality of the lyophilisates.

The object of the invention is attained by a pharmaceutical preparation containing a plasminogen activator, with the preparation containing at least one sugar and tranexamic acid as pharmaceutical additives. In lyophilised form, the preparation is stable on storage over a prolonged period of time. Likewise, the aqueous injection solution prepared by reconstitution meets this criterion of improved storage stability. In particular, this is the case when the pH value of the solution is adjusted to a value of between 5.5–6.5. As further additives, the pharmaceutical preparations may contain conventional buffer substances or surface-active materials (anionic, cationic or neutral surfactants).

As an example of the plasminogen activators (PA) possible within the meaning of the invention, the plasminogen activator K2P (BM 06.022) described in more detail in the European patent application EP-A-0 382 174 was used. It consists of the cringle 2 (K2) and the protease domain (P) of human t-PA and, due to its expression in *Escherichia coli* cells, is present in non-glycosylated form.

As sugar, the formulations of the invention preferably contain mono- or disaccharides. As the disaccharides, particularly saccharose, trehalose, maltose or lactose are possible. In particular, the monosaccharides are galactose or corresponding amino sugars such as, e.g., galactosamine. Preferably, the non-reducing sugars saccharose and trehalose are employed. The sugar concentration in the aqueous injection solution is preferably 40–100 mg/ml, with between 50–70 mg/ml being preferred.

As buffer substances, the pharmaceutical preparations may contain conventional substances possible for such purposes and representing salts of strong acids with weak bases or of weak acids with strong bases. As examples, there may be mentioned: alkali salts of phosphoric acid, tartaric acid, malic acid and the like. Amino acids are also possible. Preferably, the preparations according to the invention contain phosphate buffer. In particular, the concentration of phosphate buffer in the aqueous solution ready for injection is 50–300 mmoles/l, preferably 80–220 mmoles/l and, particularly preferred, 130–170 mmoles/l. As a phosphate buffer, disodium or dipotassium hydrogen phosphate is preferably used, which is adjusted to the respective pH value using phosphoric acid.

As solubiliser, the preparations according to the invention contain tranexamic acid (TES). The concentration of tranexamic acid in the aqueous solution ready for injection is preferred to be 1–50 mmoles/l, preferably 8–12 mmoles/l. Particularly advantageous is the use of a concentration of 10 mmoles/l. Surprisingly, tranexamic acid has been found to increase the solubility of plasminogen activators, particularly of non-glycosylated plasminogen activators in an aqueous medium. For instance, in the case of the plasminogen activator derivative r-PA, solubility was increased at least by a factor of 1.5 with respect to a solution free of tranexamic acid. The factor for the solubility increase preferably ranges from 2–3. This effect, above all, is advantageous within the scope of the preparation of lyophilised pharmaceutical preparations of plasminogen activators since, due to the possibility of increasing the concentration of the plasminogen activator in the solutions used, the amount of water to be used in the production process may be reduced significantly and, on the whole, a production is achieved which is energy-saving and more cost effective. In particular, the lyophilisation periods in the production process are reduced.

As surfactants, non-ionic, anionic or cationic surfactants, preferably, however, non-ionic surfactants such as Tween 80 or Tween 20 may be used. The surfactant concentration is 0.005–0.1% (w/v) and preferably 0.01%.

A pH value of between 5.5–6.5 is suitable for a pharmaceutical preparation in aqueous form according to the invention; a pH value of 5.8–6.2 is preferred.

The preparations of the invention contain the active substance at a concentration of up to 10 mg/ml, preferably of 3–5 mg/ml.

The pharmaceutical preparations according to the invention are employed as injection or infusion solutions. This can be done by providing a solution ready for injection, which has the composition according to the invention. However, the pharmaceutical preparations may also be provided in the form of lyophilisates. These are then reconstituted using per se known agents or solutions (e.g., with water) suitable for injections. As the injection medium, water is preferably employed for the preparations of the invention, which optionally may contain conventional isotonic additives such as a physiological concentration of NaCl.

Likewise, the invention is directed to the process of manufacturing a pharmaceutical preparation containing plasminogen activators or derivatives of same having a pH value of from 5.5 to 6.5 and their use in manufacturing the pharmaceutical preparations according to the invention.

In addition, the invention is directed to the use of a specified mixture of pharmaceutical adjuvants consisting of the group sugar and tranexamic acid for the longterm stabilisation of plasminogen activators. In particular, in order to achieve good storage stability, a combination of the adjuvants sugar, phosphate buffer, tranexamic acid, and surfactant is especially advantageous.

Examinations on stability show that the preparations according to the invention are stable as solutions for at least 30 days at 4° C. The stability of the active substance in the lyophilisates according to the invention is between two and five years at 4° C. Of particularly advantageous influence is the fact that the drug preparations have excellent stability even at increased thermal stress, which makes them largely insensitive to temperature fluctuations which, in particular, may occur in warmer climatic regions of the earth, and all the more so when the cold chain is interrupted. Due to the often long shipping routes involved in pharmaceutical forms of administration from the drug manufacturer down to the consumer in the various countries, unintended exposure of the preparations to temperature fluctuations, possibly even over a prolonged period of time, cannot be excluded, which give rise to activity loss of the protein and thus, in the extreme case, render the success of therapeutic treatment questionable. However, the pharmaceutical forms of administration according to the invention are largely insensitive to such temperature fluctuations. It has been possible to demonstrate in preliminary examinations on stability that in the preparations, even when exposed to a temperature of 35° C. over a time period of 30 days, no significant impairment regarding the stability of the protein could be detected. Therefore, the preparations must be assumed to have a stability of from two to five years when stored properly at refrigerator temperature.

Furthermore, the preparations according to the invention are advantageous in that the glass temperature (Tg') of the frozen solution for the preparation of the lyophilisates is relatively high, ranging between −33° C. and −40° C. so that the reproducibility of product quality of the lyophilisates is ensured with sufficient reliability on the production scale as well. The relatively high glass temperature is advantageous especially because if technically induced or unforeseen increases in temperature occur during the often very long lyophilisation periods, the risk of unintended thawing of the frozen solutions is less probably involved. In cases where the glass temperature is below −40° C. and that temperature is exceeded during the lyophilisation process, which is particularly the case in technical lyophilisation plants, which work at temperatures somewhat close to −45° C., the undesired exceeding of the glass temperature may cause disadvantageous changes in the frozen solution. Sufficiently good product quality is then no longer ensured. Here loss of activity of the protein, and the formation of aggregates, respectively, may occur, in particular, in the case of protein-containing lyophilisates. A further advantage in the case of the preparations according to the invention, with a glass temperature of from −33° C. to −40° C., is that the requisite expenditure of energy for the lyophilisation process is minimised because the lyophilisation procedure need not necessarily be carried out at temperatures below −50° C.

In the meaning of the present invention, relatively high glass temperatures can be attained for the frozen solutions especially when a potassium salt such as dipotassium hydrogen phosphate or potassium dihydrogen phosphate is used as the phosphate buffer for the solutions required for lyophilisation. In this regard, in particular, dipotassium hydrogen phosphate at a concentration of from 20–40 mg/ml, preferably 20–30 mg/ml can be used. The increase in glass temperature can be enhanced by adding saccharose. In this connection, saccharose is added preferably at a concentration of from 60–90 mg/ml, in particular, 60–80 mg/ml. The use of a solution containing about 26 mg/ml of dipotassium hydrogen phosphate ($K_2HPO_4 \times 12\ H_2O$) and about 70 mg/ml of saccharose is particularly preferred. The pH value of the solution is adjusted to a value of 6 using, preferably, 85%-phosphoric acid (about 12 mg/ml). The solution further contains about 0.5–5 mg/ml, preferably 1–2 mg/ml tranexamic acid, in particular, about 1.6 mg/ml. Besides this, the solution may contain, in addition, surfactants such as Tween 80, which is applied preferably at a concentration of from 0.01–0.3 mg/ml, in particular, about 0.1 mg/ml.

Another advantage of the lyophilisates according to the invention is that on completion of the lyophilisation they exhibit a relatively low residual moisture. The residual moisture is, in particular, at values below 5%, preferably ranging between 0.5–4%, in particular, 1–3%. The values for lyophilisates usually are at levels above 6%. The low residual moisture contributes to the improved storage stability of the preparations. Preparations having a higher residual moisture often result in instability of the protein, which becomes apparent from the loss of biological activity or the formation of aggregates.

Another advantage of the preparation according to the invention is that when producing the lyophilisates, due to the increase in solubility of non-glycosylated plasminogen activators, in particular, in the case of the type K2P, K1K2P or P type muteins, achieved by the addition of tranexamic acid, one may start with smaller volumes (for example, of about 5 ml per single administration form) of solutions to be frozen, so that the lyophilisation period is significantly reduced with respect to solutions hitherto used for the preparation of lyophilisates (for example, of about 10 ml per administration form). Preferably, one starts with solutions containing the active substance at a concentration about twice as high as compared to the aqueous administration form ready for injection so that aqueous solutions of 5 ml can be used instead of the hitherto conventional solutions of 10 ml. "It is most preferred where, prior to lyophilization, the aqueous solution contains the active substance at a concentration which is up to three times higher than the concentration of a ready-to-use aqueous injection or infusion solution."

Examinations on venous tolerance demonstrate very good tolerance of the preparations according to the invention.

Without limiting, the following embodiments are intended to illustrate the invention in more detail.

EXAMPLE 1

Clouding on Mechanical Stress/Measurement of Light Scattering of Preparations According to the Invention r-PA (BM 06.022) was adjusted to a protein concentration ($C_{prot.}$) of 6 mg/ml (ultrafiltration over an Amicon YM 10 membrane) and dialysed against the buffers as indicated. Subsequently, the samples were adjusted to $C_{prot.}=4$ mg/ml and were a) left unchanged, b) filled up with 0.01% Tween 80, and c) with 0.01% Tween 20.

Exposing each of the samples to stress was effected for 10 s on a Whirl Mix (Janke & Kunkel, IKA Labortechnik VF2, maximum rotational speed). Subsequently, the samples were incubated for 2 minutes at room temperature.

Light scattering of the unstressed and stressed samples was measured by fluorimetry at 25° C. (Ex. 360 nm, Em.: 360 nm; Ex. bandpath: 3 nm; Em. bandpath: 10 nm; measuring intervals: 10 s over 3 min). In FIG. 1 the values for the scattering of the samples are given, each one corrected by the fluorescence of the buffer.

Result:

The present data shows that without addition of detergents, there is substantial increase in light scattering of the sample under mechanical stress (FIG. 1). By adding detergents, the increase can be suppressed to the largest extent. Within the scope of measuring accuracy, no difference between Tween 80 and Tween 20 is notable.

In FIG. 1 (mechanical stressing of samples A, B, C, D) the obtained results are summarised. The meanings of each of the abbreviations used in FIG. 1 are as follows:

| | |
|---|---|
| A) | 150 mM of $Na_2HPO_4/H_3PO_4$, pH 6.0 |
| | 10 mM of TES |
| | 50 mg/ml of saccharose |
| | a) without detergent |
| | b) with 0.01% of Tween 80 |
| | c) with 0.01% of Tween 20 |
| B) | 150 mM of $Na_2HPO_4/H_3PO_4$, pH 6.0 |
| | 10 mM of TES |
| | 50 mg/ml of trehalose |
| | a) without detergent |
| | b) with 0.01% of Tween 80 |
| | c) with 0.01% of Tween 20 |
| C) | 150 mM of $K_2HPO_4/H_3PO_4$, pH 6.0 |
| | 10 mM of TES |
| | 50 mg/ml of saccharose |
| | a) without detergent |
| | b) with 0.01% of Tween 80 |
| | c) with 0.01% of Tween 20 |
| D) | 150 mM of $K_2HPO_4/H_3PO_4$, pH 6.0 |
| | 10 mM of TES |
| | 50 mg/ml of trehalose |
| | a) without detergent |
| | b) with 0.01% of Tween 80 |
| | c) with 0.01% of Tween 20 |

EXAMPLE 2

Storage of r-PA (BM 06.022) in TES/Saccharose-Containing Formulations According to the Invention//Multiple Freezing and Thawing r-PA was dialysed against the buffer (without Tween 80) indicated in Table 1, adjusted to $C_{prot.}=4$ mg/ml, filled up with Tween 80 to C=0.01%, portioned, and sterile filtrated. Each time 9 samples were frozen at −20° and −70° C., respectively. On the days as indicated in the Table all of the samples were thawed (15 min at 25° C. in a water bath) except for the control. Each time one sample was analysed ($C_{prot.}$ and amidolytic activity). The rest of the samples were frozen at −20° C. and −70° C., respectively. After completion of the series the activity of the non-stressed sample was determined.

Result:

As it is apparent from the data in Table 1, r-PA may be frozen and thawed at least eight times without loss of activity.

TABLE 1

150 mM of $Na_2HPO_4/H_3PO_4$, pH 6.0
10 mM of TES
50 mg/ml of saccharose
0.01% of Tween 80

| | −20° C. | | −70° C. | |
|---|---|---|---|---|
| Day | $C_{prot.}$ [mg/ml] | AA [MU/ml] | $C_{prot.}$ [mg/ml] | AA [MU/ml] |
| 0 | 4.1 | 3.1 | 4.1 | 3.1 |
| 1 | 4.5 | 3.1 | 4.6 | 3.0 |
| 2 | 4.6 | 3.2 | 4.8 | 3.1 |
| 3 | 4.3 | 3.1 | 4.0 | 3.0 |
| 4 | 4.8 | 3.1 | 4.7 | 3.1 |
| 5 | 4.1 | 3.3 | 4.1 | 3.2 |
| 6 | 4.2 | 3.0 | 4.2 | 3.1 |
| 7 | 4.1 | 3.1 | 4.3 | 3.2 |
| 8 | 4.0 | 2.9 | 4.3 | 3.1 |
| Control | 4.3 | 3.0 | 4.3 | 3.1 |

Control: Untreated sample measured
AA: Amidolytic activity
$C_{prot.}$: Protein concentration

EXAMPLE 3

Stability of r-PA in Solution

Comparison of Various Formulations at $C_{prot.}=4$ mg/ml r-PA (BM 06.022) was concentrated over an Amicon YM 10 membrane to 5 mg/ml and dialysed against the buffer (without Tween 80) indicated in Table 2. The dialysates were adjusted to $C_{prot.}=4$ mg/ml, filled up with Tween 80 to C=0.01%, portioned, and stored at −20° C. and 4° C. After 7, 14, 20 and 30 days, amidolytic activity and protein concentration of the stressed samples were determined.

Result:

The samples stored at −20° C. and 4° C. remain unchanged over 30 days.

TABLE 2

150 mM of $Na_2HPO_4/H_3PO_4$, pH 6.0
10 mM of TES
50 mg/ml of trehalose
0.01% of Tween 80

| | −20° C. | | +4° C. | |
|---|---|---|---|---|
| Day | $C_{prot.}$ [mg/ml] | AA [MU/ml] | $C_{prot.}$ [mg/ml] | AA [MU/ml] |
| 0 | 3.9 | 2.1 | | |
| 7 | 3.9 | 2.3 | 3.97 | 2.4 |
| 14 | 3.9 | 2.3 | 3.98 | 2.4 |
| 20 | 3.9 | 2.3 | 3.9 | 2.4 |
| 30 | 3.9 | 2.3 | 3.9 | 2.4 |

AA: Amidolytic activity $C_{prot.}$: Protein concentration

EXAMPLE 4

Stability of r-PA in Solution

Comparison of Various Formulations at $C_{prot.}=6$ mg/ml r-PA (BM 06.022) was dialysed overnight against the buffers indicated below and adjusted to $C_{prot.}=6$ mg/ml by concentrating over an Amicon YM 10 membrane. The samples were filled into portions of 1 ml and stored for 30 days at −20° C. and 4° C. After 1, 2, 5, 9, 15 and 29 days amidolytic activity and protein level were determined each time.

TABLE 3

200 mM of $Na_2HPO_4/H_3PO_4$, pH 6.0
10 mM of TES
50 mg/ml of saccharose
0.01% of Tween 80

| | −20° C. | | +4° C. | |
|---|---|---|---|---|
| Day | $C_{prot.}$ [mg/ml] | AA [MU/ml] | $C_{prot.}$ [mg/ml] | AA [MU/ml] |
| 0 | 6.0 | 3.3 | 6.0 | 3.3 |
| 1 | 5.7 | 3.3 | 5.7 | 3.6 |
| 2 | 5.8 | 3.3 | 5.9 | 3.4 |
| 5 | 5.9 | 3.2 | 6.0 | 3.6 |
| 9 | 6.0 | 3.3 | 5.9 | 3.7 |
| 15 | 5.8 | 3.5 | 5.9 | 3.5 |
| 29 | 5.9 | 3.6 | 5.9 | 3.8 |

AA: Amidolytic activity $C_{prot.}$: Protein concentration

TABLE 4

150 mM of $Na_2HPO_4/H_3PO_4$, pH 6.0
10 mM of TES
50 mg/ml of saccharose
0.01% of Tween 80

| | −20° C. | | −70° C. | |
|---|---|---|---|---|
| Day | $C_{prot.}$ [mg/ml] | AA [MU/ml] | $C_{prot.}$ [mg/ml] | AA [MU/ml] |
| 0 | 5.9 | 3.5 | 5.9 | 3.5 |
| 1 | 5.5 | 3.5 | 5.6 | 3.4 |
| 2 | 5.6 | 3.4 | 5.5 | 3.5 |
| 5 | 6.0 | 3.5 | 6.2 | 3.6 |
| 9 | 6.0 | 3.3 | 6.0 | 3.3 |
| 15 | 6.0 | 3.6 | 5.9 | 3.1 |
| 29 | 5.9 | 3.5 | 6.0 | 3.6 |

AA: Amidolytic activity $C_{prot.}$: Protein concentration

Result:

The Tables indicate that the active substance BM 06.022 in the formulations mentioned is stable for at least 29 days at −20° C. and 4° C.

EXAMPLE 5
Solubility of r-PA in the Formulations of the Invention r-PA (BM 06.022) was concentrated to 6 mg/ml over YM 10 and dialysed against the buffer indicated below. The dialysates in turn were concentrated over an Amicon YM 10 membrane until clouding occurred. Following centrifugation of the samples, the supernatants were stored for five days at 4° C. Amidolytic activity and $C_{prot.}$ were determined at the beginning and the end of storage.

TABLE 5

| 150 mM of Na₂HPO₄/H₃PO₄, pH 6.0 |||
| 10 mM of TES |||
| 50 mg/ml of saccharose |||
| 0.01% of Tween 80 |||
| Day | $C_{prot.}$ [mg/ml] | AA [MU/ml] |
| --- | --- | --- |
| 0 | 10.2 | 4.8 |
| 5 | 10.2 | 4.9 |

AA: Amidolytic activity $C_{prot.}$: Protein concentration

Result:

The solubility of r-PA is about 10 mg/ml. At maximum protein concentration the sample may be stored at least for up to 5 days at 4° C. without change in amidolytic activity.

EXAMPLE 6
Preparation of Liquid Administration Forms

The following administration forms were prepared as solutions prior to lyophilisation:

Composition of the solutions prior to lyophilisation

| Solution A: | |
| --- | --- |
| BM 06.022 | 4 mg/ml |
| Na₂HPO₄·12H₂O | 53.72 mg/ml |
| H₃PO₄ 85% | 11.3 mg/ml |
| Tranexamic acid | 1.6 mg/ml |
| Saccharose | 50 mg/ml |
| Tween 80, pH 6 | 0.1 mg/ml |
| Solution B: | |
| BM 06.022 | 4 mg/ml |
| K₂HPO₄ | 26.2 mg/ml |
| H₃PO₄ 85% | 11.6 mg/ml |
| Tranexamic acid | 1.6 mg/ml |
| Saccharose | 70 mg/ml |
| Tween 80, pH 6 | 0.1 mg/ml |

Preparation of the Lyophilisates:

Following sterile filtration, aliquots of each 5 ml are filled into 20 ml glass vials. The lyophilisation is conducted as follows: The filled glass vials are placed in a freeze drier and frozen for 10 hours at temperatures of from −40° to −50° C. plate temperature and atmospheric pressure. Subsequently, a vacuum value of p=0.01 to 1 mbar is applied to the chamber. Thereafter, the plate temperature is adjusted so that at any time the product temperature will be reliably below the respective glass transition temperature. Once the total amount of ice has sublimed off, the plate temperature is raised to a value of 20°–40° C. and subsequently, an afterdrying is carried out in a vacuum. The residual moisture was determined according to conventional methods (determination according to the method of Karl Fischer) and is 6% for solution A, and 3% for solution B. Storage of the lyophilisates for examinations on stability is conducted at temperatures of 4° C. (refrigerator temperature), 20° C. (room temperature) and 35° C. Stability of the lyophilisates after a storage period of four to twelve weeks is met at the indicated temperatures as it is apparent from the analytical examinations regarding amidolytic activity and protein concentration.

Reconstitution of the lyophilisates for application:

The lyophilisates are filled up to 10 ml with water for injections. This corresponds to a dilution by a factor of two in relation to the original volume of the solution prior to lyophilisation.

EXAMPLE 7
Test on Venous Tolerance of the Formulations of the Invention

Two real solutions and two placebo solutions having the compositions listed in Table 6 were prepared and administered intravenously to rabbits. An application amount of 0.5 ml/animal was used; five animals were used for each of the four test solutions.

TABLE 6

| Composition of Real and Placebo Solutions |||
| --- | --- | --- |
| 1. Real Solutions | Test No. 93/1292 | Test No. 93/1294 |
| BM 06.022 | 10 MU | 10 MU |
| Dipotassium hydrogen phosphate | 131.0 mg | 131.0 mg |
| Phosphoric acid 85% | 58 mg | 58 mg |
| Tranexamic acid | 8.0 mg | 8.0 mg |
| Saccharose | 250.0 mg | 350.0 mg |
| Polysorbate 80 | 0.5 mg | 0.5 mg |
| Water p.i. | q.s. 10.0 ml | q.s. 10.0 ml |
| pH | 6.0 | 6.0 |
| Osmolarity | 320 mOsmoles | 351 mOsmoles |
| 2. Placebo Solutions | Test No. 93/1291 | Test No. 93/1293 |
| Dipotassium hydrogen phosphate | 131.0 mg | 131.0 mg |
| Phosphoric acid 85% | 58 mg | 58 mg |
| Tranexamic acid | 8.0 mg | 8.0 mg |
| Saccharose | 250.0 mg | 350.0 mg |
| Polysorbate 80 | 0.5 mg | 0.5 mg |
| Water p.i. | q.s. 10.0 ml | q.s. 10.0 ml |
| pH | 6.0 | 6.0 |
| Osmolarity | 322 mOsmoles | 343 mOsmoles |

Result:

The animals' reactions on injection and the histological findings demonstrate that all of the employed test solutions are well tolerated.

We claim:

1. A pharmaceutical composition comprising a protein having plasminogen activator activity, sugar and tranexamic acid, wherein said tranexamic acid is the only aminocarboxylic acid in said composition, and wherein said composition is devoid of citrate.

2. The composition according to claim 1, wherein said sugar is a disaccharide.

3. The preparation according to claim 2, wherein said disaccharide is saccharose or trehalose.

4. The composition according to claim 1, further comprising a buffer, wherein said buffer comprises a potassium salt of phosphoric acid.

5. The composition according to claim 4, wherein said potassium salt of phosphoric acid is dipotassium hydrogen phosphate.

6. The composition according to claim 4, wherein said buffer is 50–300 mmoles/l of phosphate buffer.

7. The composition according to claim 6, wherein said buffer is 80–220 mmoles/l of phosphate buffer.

8. The composition according to claim 1, wherein said composition is in the form of a frozen solution.

9. The composition according to claim 1, wherein said sugar is present in an amount of 40–100 mg/ml.

10. The composition according to claim 7, wherein said sugar is present in an amount of 50–70 mg/ml.

11. The composition according to claim 1, wherein said tranexamic acid is present in an amount of 1–50 mmoles/l.

12. The composition according to claim 11, wherein said tranexamic acid is present in an amount of 8–12 mmoles/l.

13. The composition according to claim 1, further comprising 0.005–01% of a surfactant.

14. The composition according to claim 13, wherein said surfactant is present in an amount of 0.01%.

15. The composition according to claim 1, wherein said protein having plasminogen activator activity is a K2P type recombinant protein having plasminogen activator activity.

16. The composition according to claim 15, wherein said K2P type recombinant protein having plasminogen activator activity is BM 06.022.

17. The composition according to claim 1, wherein said protein having plasminogen activator activity is t-PA at a concentration of up to 10 mg/ml.

18. The composition according to claim 1, wherein said composition is a lyophilizate.

19. The composition according to claim 1, wherein said composition is an aqueous solution and the pH value of the solution is 5.5–6.5.

20. The composition according to claim 1, wherein said composition has a storage stability of 30 days at a temperature of 35° C.

21. A composition in the form of a lyophilisate with a residual moisture content of less than 5%, comprising a protein having plasminogen activator activity, sugar, phosphate buffer, tranexamic acid and a surfactant, wherein said composition is devoid of citrate and wherein said tranexamic acid is the only aminocarboxylic acid in said composition.

22. The composition according to claim 21, wherein said lyophilisate has a residual moisture between 1–3%.

23. The composition according to claim 21, wherein said composition has a storage stability of 30 days at a temperature of 35° C.

24. A process for preventing the loss of plasminogen activator activity or for preventing the formation of protein aggregates in a composition which contains a protein having plasminogen activator activity, comprising mixing said protein having plasminogen activator activity with sugar and tranexamic acid, wherein said tranexamic acid is the only aminocarboxylic acid in said composition, and wherein said composition is devoid of citrate.

25. A process for preparing a lyophilized pharmaceutical composition comprising a protein having plasminogen activator activity, sugar and tranexamic acid, wherein said tranexamic acid is the only aminocarboxylic acid in said composition, and wherein said composition is devoid of citrate, comprising preparing an aqueous solution containing a protein having plasminogen activator activity, sugar, and tranexamic acid, freezing the aqueous solution, adjusting the temperature of the frozen solution to a value below the glass temperature, and lyophilizing the frozen solution in a vacuum.

26. The method according to claim 25, wherein said temperature is adjusted to between −40° C. and −50° C.

27. The process according to claim 25, wherein prior to lyophilization the aqueous solution contains the protein having plasminogen activator activity at a concentration which is up to three times higher than the concentration of a ready-to-use aqueous injection or infusion solution.

28. A method for treating blood clots comprising administering to a patient in need of such treatment, an effective amount of a composition comprising an effective amount of a protein having plasminogen activator activity, sugar and tranexamic acid, wherein said tranexamic acid is the only aminocarboxylic acid in said composition, said composition is devoid of citrate and wherein said composition is in a vein-tolerated pharmaceutical administration form.

29. A pharmaceutical composition comprising a protein having plasminogen activator activity, sugar and a single aminocarboxylic acid, wherein said single aminocarboxylic acid is tranexamic acid, and wherein said composition is devoid of citrate.

* * * * *